United States Patent
Barnard

(10) Patent No.: US 9,526,832 B1
(45) Date of Patent: Dec. 27, 2016

(54) HAND STRAP FOR PATIENT CONTROLLED ANALGESIA CONTROL

(71) Applicant: atHand Medical Inc., Greensboro, NC (US)

(72) Inventor: Stephanie Barnard, Wilson, NC (US)

(73) Assignee: atHand Medical Inc., Greensboro, NC (US)

( * ) Notice: Subject to any disclaimer, the term of this patent is extended or adjusted under 35 U.S.C. 154(b) by 0 days.

(21) Appl. No.: 14/695,074

(22) Filed: Apr. 24, 2015

Related U.S. Application Data

(63) Continuation-in-part of application No. 14/509,814, filed on Oct. 8, 2014.

(51) Int. Cl.
*A61M 5/172* (2006.01)
*A45F 5/00* (2006.01)
*A61M 5/14* (2006.01)
*A61M 5/168* (2006.01)

(52) U.S. Cl.
CPC .......... *A61M 5/172* (2013.01); *A45F 5/00* (2013.01); *A45F 2005/008* (2013.01); *A61M 5/16804* (2013.01); *A61M 2005/1405* (2013.01); *A61M 2205/586* (2013.01); *A61M 2209/088* (2013.01)

(58) Field of Classification Search
CPC ............ A61M 5/16804; A61M 2205/586; A61M 2209/088; A61M 2005/1405; A61M 5/172; A45F 5/00; A45F 2005/008
See application file for complete search history.

(56) References Cited

U.S. PATENT DOCUMENTS

| | | | |
|---|---|---|---|
| 4,569,348 A | 2/1986 | Hasslinger | |
| 4,836,427 A * | 6/1989 | McManus | A45F 5/00 224/247 |
| 4,862,563 A | 9/1989 | Flynn | |
| 5,104,076 A | 4/1992 | Goodall, Jr. | |
| 5,131,118 A | 7/1992 | Breeher | |
| 5,174,483 A | 12/1992 | Moore, IV et al. | |
| 5,582,337 A * | 12/1996 | McPherson | A45F 3/14 224/660 |
| 5,820,000 A * | 10/1998 | Timberlake | A01M 31/004 224/219 |
| 6,708,375 B1 * | 3/2004 | Johnson | A44B 15/005 24/17 A |
| 7,137,480 B2 * | 11/2006 | Williams | A01M 31/02 182/187 |

(Continued)

FOREIGN PATENT DOCUMENTS

WO    0160192 A1    8/2001

OTHER PUBLICATIONS

Information Disclosure Statement (IDS) Letter Regarding Common Patent Application(s) dated Jun. 8, 2016.

(Continued)

*Primary Examiner* — Robert J Sandy
*Assistant Examiner* — Louis Mercado
(74) *Attorney, Agent, or Firm* — Tillman Wright, PLLC; James D. Wright; David R. Higgins

(57) ABSTRACT

Clips or straps may be used to position a patient-controlled-analgesia (PCA) pump control in a position where a patient can easily operate a PCA pump. A strap that allows a PCA pump control to always be in hand or very close at hand is preferable to a strap or clip that merely keeps a PCA pump control nearby.

20 Claims, 4 Drawing Sheets

(56) References Cited

U.S. PATENT DOCUMENTS

| | | | |
|---|---|---|---|
| 7,640,632 B2 | 1/2010 | Lazarus | |
| 8,573,458 B1 | 11/2013 | Hamilton | |
| 2002/0084295 A1* | 7/2002 | Martindale | A45C 1/04 |
| | | | 224/219 |
| 2002/0092138 A1* | 7/2002 | Spiller | A01K 27/001 |
| | | | 24/306 |
| 2003/0121944 A1* | 7/2003 | Scanlan | A45C 13/30 |
| | | | 224/409 |
| 2008/0296325 A1* | 12/2008 | Tepper | A45F 5/00 |
| | | | 224/148.6 |
| 2009/0251101 A1 | 10/2009 | Phillips et al. | |
| 2010/0137806 A1* | 6/2010 | McCluskey | A61M 5/1418 |
| | | | 604/179 |
| 2012/0097157 A1* | 4/2012 | Cortez, Jr. | A61M 16/0875 |
| | | | 128/202.13 |
| 2013/0014354 A1 | 1/2013 | Robbins | |

OTHER PUBLICATIONS

Information Disclosure Statement (IDS) Letter Regarding Common Patent Application(s), dated Apr. 15, 2016.

\* cited by examiner

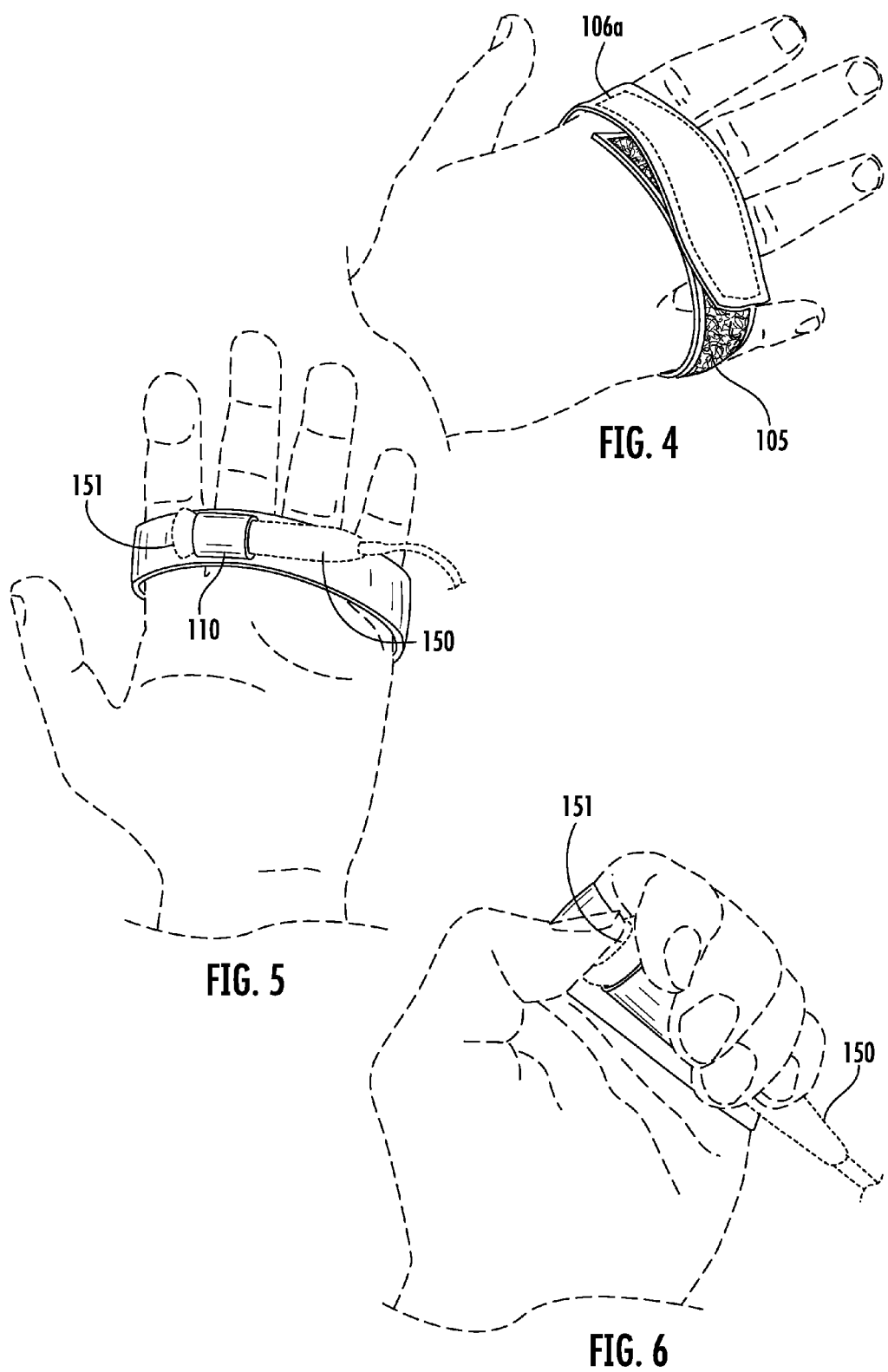

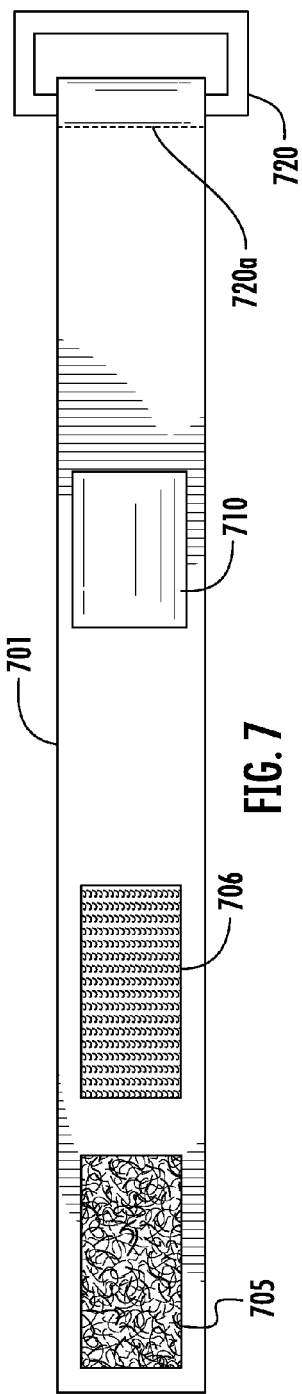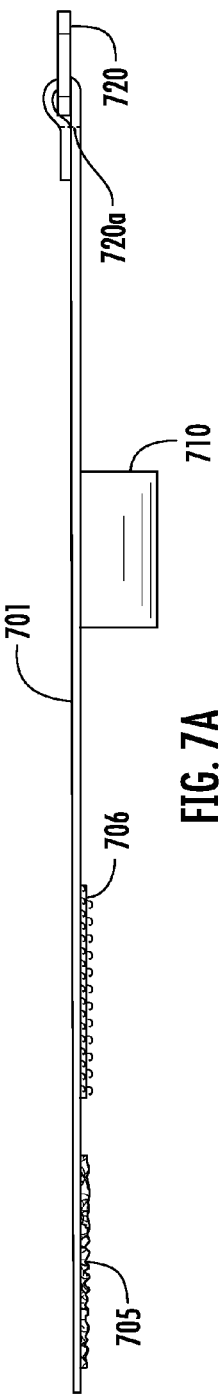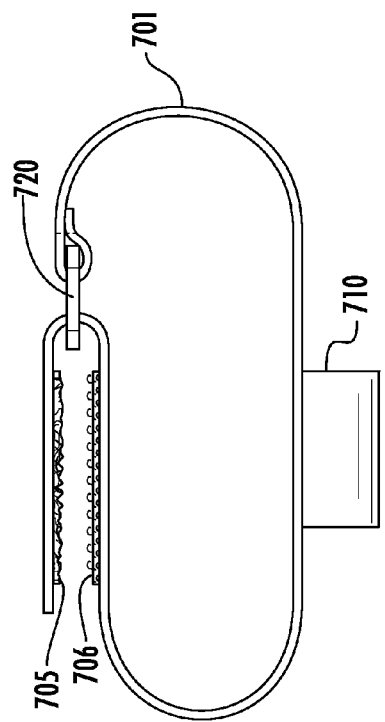
FIG. 7
FIG. 7A
FIG. 7B

HAND STRAP FOR PATIENT CONTROLLED ANALGESIA CONTROL

CROSS-REFERENCE TO RELATED APPLICATION

The present application is a U.S. non-provisional patent application of, and claims priority under 35 U.S.C. §119(e) to, U.S. provisional patent application Ser. No. 61/891,553 filed Oct. 16, 2013, which provisional patent application is incorporated by reference herein. This application is also a continuation-in-part of U.S. patent application Ser. No. 14/509,814 filed Oct. 8, 2014.

COPYRIGHT STATEMENT

All of the material in this patent document is subject to copyright protection under the copyright laws of the United States and of other countries. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

Field of the Invention

The present invention relates generally to a hand strap for use by a patient to hold a control used to operate a patient controlled analgesia (PCA) pump. A PCA pump is a device that is used to allow a patient to self-administer pain medicine, and is often used by post-operative patients or individuals who suffer from chronic pain. The pump is typically attached to an intravenous (IV) line that is inserted into a suitable vein. The purpose of a PCA pump is to allow a patient to manage their own pain control by self-administering regular doses of medicine, while preventing such a patient from self-administering an overdose of medicine. The PCA pump is generally programmed to administer a prescribed amount of medicine during a specific period of time. The PCA pump control allows the patient to have access to an allotment of pain medicine that is made available periodically, while preventing the possibility of overdose. The patient may access a portion of, or all of, each periodic allotment by manually operating the PCA pump control. The use of a PCA pump typically requires the patient to hold a PCA pump control in their hand, and to then depress a button to start the flow of pain medication. The difficulty with most PCA pump controls is that the patient needs to either hold the control for long periods of time, or be able to easily find the PCA pump control when a dose of medicine is desired.

For some patients, reduced mobility of the limbs and hands can make it extremely difficult to easily grasp the PCA pump control or hold the control for long periods of time. Such reduced mobility may be due to a post-operative condition, or may be a chronic condition due to illness, disease, or aging. If the pump control is not readily and easily accessible, it can be difficult or impossible for some patients to use the pump control, which defeats the purpose of a PCA pump. Not having ready access to pain medicine when needed may significantly slow or impede patient recovery, resulting in longer hospital stays and increased health care costs.

While there are prior art solutions for keeping the control close at hand, the majority of such solutions involve keeping the pump control within reach, but not necessarily close at hand. A need exists for improvement in the field of devices for keeping a PCA pump control at hand and to address the shortcomings of the prior art. This and other needs are addressed by one or more aspects of the present invention.

Description of Related Art

The most common type of PCA pump control is a hand grip with a push button, with the hand grip attached to the end of a cord. The preferred type of hand grip is shaped in a manner to fit the palm or across the base of the fingers of a patient's hand, allowing a patient to use the PCA pump control with minimal effort. In some instances, a patient may be too weak to hold a hand grip for any length of time, or the patient may be unable to move adequately to grab the hand grip if it falls from their hand. The most common means for keeping a PCA control device readily available to a patient is to affix a strap or clip to the cord of a PCA pump control device. In the case of a strap, the PCA pump control cord may be strapped to a bedside rail or similar article. In the case of a clip, the clip is attached to the PCA pump control cord, which is then clipped to the patient's bedclothes, bedding or other article. In either case, the attachment means helps to keep the PCA pump control within easy reach, but not necessarily at hand. A patient may be able to locate the PCA pump control when needed, or may be too weak or too immobilized to reach or hold the PCA pump control when needed. Therefore, it is an objective of the present invention to create a device for keeping a PCA pump control close at hand.

SUMMARY OF THE INVENTION

The strap of the present invention accomplishes the above objectives as described below.

In one embodiment of the present invention, the strap comprises a first band that can be worn on a patient's hand, and a second band that holds the PCA pump control in place. The second band may be elastic to allow a PCA pump control to be held in place by the stretch of the elastic, or it may comprise fabric tapes that can be wrapped around the control and fastened by means such as Velcro® or other means. The first band may be elastic to fit over a patient's hand to be held in place by the stretch of the elastic, or it may comprise fabric tapes that can be wrapped around the hand and fastened together by means such as Velcro® or other means. The first band should ideally incorporate elastic materials in either embodiment to ensure that the band fits comfortably around the patient's hand. The use of elastic materials allows the strap of the present invention to adjust to different size hands, as well as to accommodate different size PCA pump control grips. The first band is fastened to the second band in a manner that ensures that the grip of the PCA pump control is positioned in a manner that allows that the patient to quickly and easily push a button with minimal exertion and dexterity.

In one embodiment of the present invention, the strap comprises a first band that can be worn on a patient's hand, and a second band that holds the PCA pump control in place. The second band may be elastic to allow a PCA pump control to be held in place by the stretch of the elastic, or it may comprise fabric tapes that can be wrapped around the control and fastened by means such as Velcro® or other means. The first band may be elastic to fit over a patient's hand to be held in place by the stretch of the elastic, or it may comprise fabric tapes that can be wrapped around the hand and fastened together by means such as Velcro® or other means. The first band should ideally incorporate elastic materials in either embodiment to ensure that the band fits comfortably around the patient's hand. The use of elastic materials allows the strap of the present invention to adjust to different size hands, as well as to accommodate different size PCA pump control grips. The first band is fastened to the second band in a manner that ensures that the grip of the PCA pump control is positioned in a manner that allows that the patient to quickly and easily push a button with minimal exertion and dexterity.

BRIEF DESCRIPTION OF THE DRAWINGS

One or more preferred embodiments of the present invention now will be described in detail with reference to the accompanying drawings, wherein the same elements are referred to with the same reference numerals.

FIG. 4 shows the first band of the strap of the present invention fastened about a hand;

FIG. 5 shows another view of the strap of the present invention fastened about a hand with a PCA pump control:

FIG. 6 shows a PCA pump control and the strap wherein the pump control user is depressing a button;

FIG. 7 is an illustration of a front view of a strap for a PCA pump control;

FIG. 7A is an illustration of a side view of a strap for a PCA pump control; and FIG. 7B is an illustration of a different side view of a strap for a PCA pump control.

DETAILED DESCRIPTION

Figure 1:
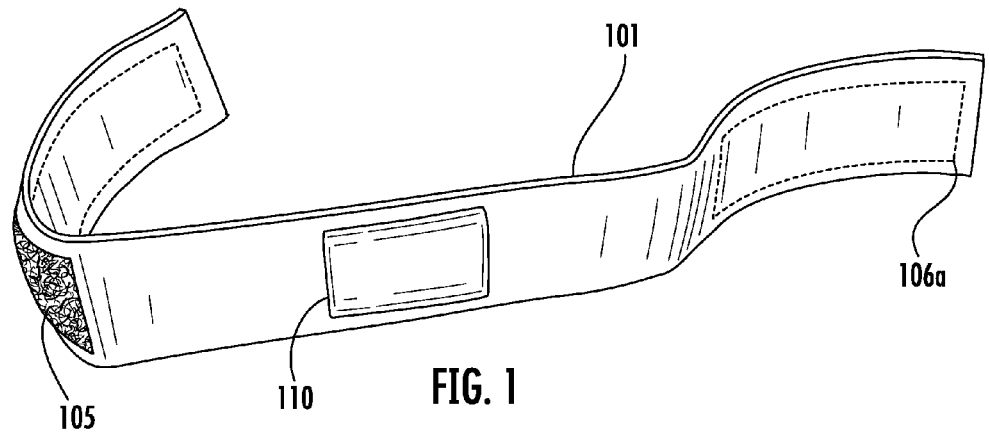
FIG. 1 is an illustration of a strap for a PCA pump control shown in perspective.

As a preliminary matter, it will readily be understood by one having ordinary skill in the relevant art (an "Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended to, nor is to be construed to, limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

In a preferred embodiment, the strap of the present invention is comprised of flexible materials and a hook-and-loop fastening means such as Velcro®, although other fastening means may be used, including without limitation snap fasteners.

FIG. 1 is an illustration of a strap for a PCA pump control shown in perspective. The strap is comprised of a first band 101 and a second band 110 that is affixed to the first band 101. A piece of a loop tape 105 of a hook-and-loop fastener is sewn to one end of the outside surface (the surface that does not contact the patient's hand) of the first band 101, and a piece of hook tape 106 is sewn to the inside surface (the surface that contacts the patient's hand) of the other end of first band 101. FIG. 1 does not show a piece of hook tape 106, but does illustrate stitching 106a that is used to attach the hook tape to first band 101. The first band 101 may be made from any number of materials, but is preferably made from an elastic fabric material.

The second band 110 may also be made from any number of materials. In one embodiment of the present invention, the second band 110 is made from an elastic fabric formed into a loop and sewn to first band 101. In another embodiment, the second band is made from an elastic fabric material, with one end sewn to the first band 101 and the other end loose. The loose end may have a piece of a loop tape of a hook-and-loop fastener that is sewn to the loose end of second band 110 that is suitably enabled to mate with a piece of hook tape that is sewn to the back side of first band 101. In another embodiment, the second band is made from an inelastic fabric material, with one end sewn to the first band 101 and the other end loose. The loose end may have one half of a snap fastener crimped to the loose end of second band 110 that is suitably enabled to mate with a matching snap fastener half that is crimped to the back side of first band 101.

Figure 2:
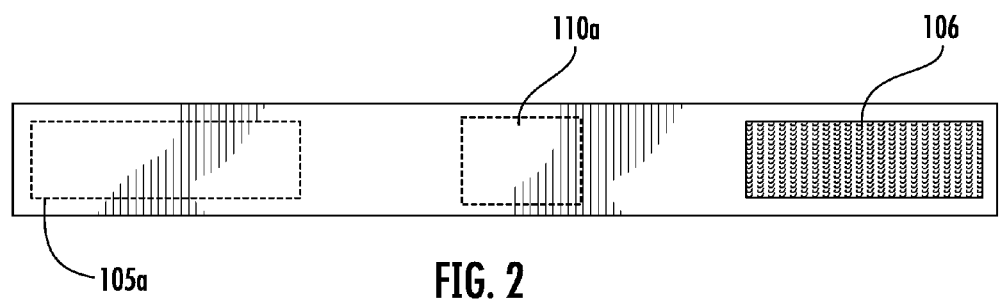
FIG. 2 is an illustration of a back view of a strap for a PCA pump control.

FIG. 2 is an illustration of a back view of a strap for a PCA pump control. In this view, the stitching 105a for a piece of a loop tape 105 of a hook-and-loop fastener is shown on one end of first band 101, and a piece of hook tape 106 is sewn to the other end of first band 101. The stitching 110a affixing second band 110 to the middle of first band 101 is also shown.

Figure 3:
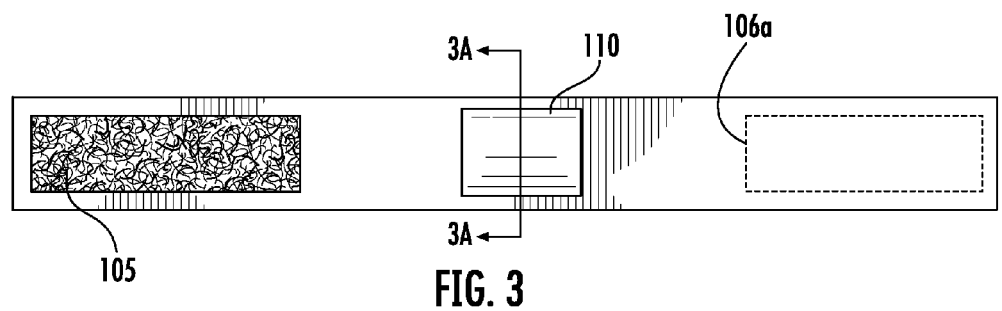
FIG. 3 is an illustration of a front view of a strap for a PCA pump control.

FIG. 3 is an illustration of a front view of a strap for a PCA pump control. In this view, the stitching 106a for a piece of a hook tape 106 of a hook-and-loop fastener is shown on the end of first band 101, opposite the end with hook tape 105. The second band 110 is also shown affixed to the middle of the longitudinal length of the first band 101. While stitching in FIG. 1 and FIG. 2 is shown for affixing a piece of loop tape 105, a piece of hook tape 106, and second band 110 to first band 101, it is understood that other affixing means such as adhesives and the like may be used. It is further understood that the positions of the loop tape 105 and hook tape 106 may be reversed.

Figure 3A:
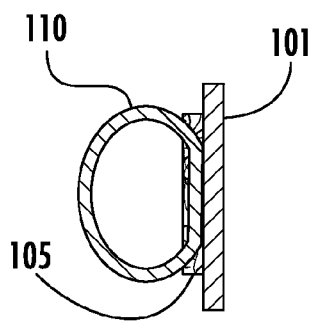
FIG. 3A is a section view of a strap for a PCA pump control.

FIG. 3a illustrates a section view of a strap for a PCA pump control hand grip, where second loop 110 is shown affixed to the outer surface of first band 101. The size of second loop 110 may vary based on its intended use, but is preferably made from an elastic fabric to accommodate a variety of PCA pump control hand grips. The use of elastic fabric allows a variety of sizes of PCA pump control hand grips to be easily but securely inserted through second loop 110, and the stretch of the elastic fabric can hold the PCA pump control hand grip securely in a desired position.

Figure 3B:
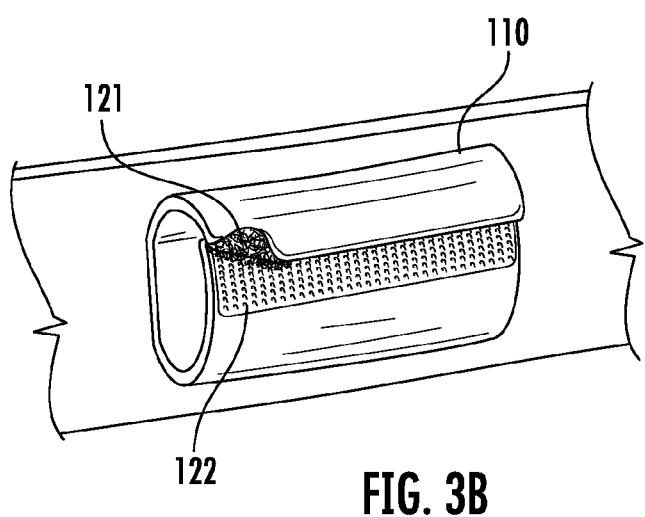
FIG. 3B is a perspective view of the second band incorporating a hook-and-loop closure for a PCA pump control.

FIG. 3b illustrates a section view of an alternate strap for a PCA pump control hand grip. In this embodiment of the present invention, the second band 110 is made from an elastic or inelastic fabric material, with a center section of second band 110 sewn to the first band 101, but with both ends loose. A piece of a loop tape 121 and a piece of hook tape 122 is affixed (by sewing, adhesive, or other fastening means) to the respective loose ends of second band 110 in a manner that allows the ends of second band 110 to be wrapped around a PCA pump control hand grip and held securely in place by mating the ends of the hook and loop tapes of the hook-and-loop fastener. The hook tape 122 and loop tape 121 may be reversed.

Figure 3C:
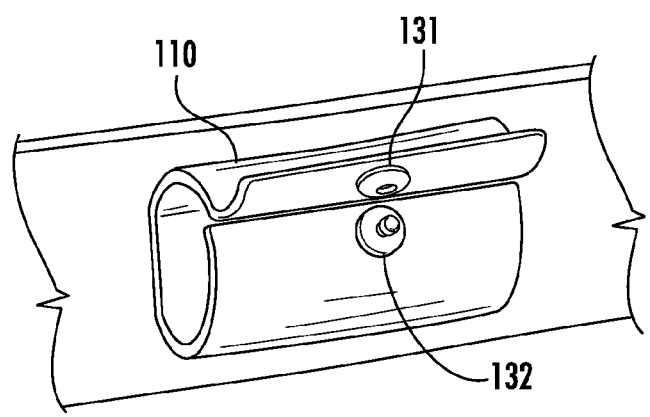
FIG. 3C is a perspective view of the second band incorporating a snap closure for a PCA pump control.

FIG. 3c illustrates a section view of an alternate strap for a PCA pump control hand grip. In this embodiment of the present invention, the second band 110 is made from an elastic or inelastic fabric material, with a center section of second band 110 sewn to the first band 101, but with both ends loose. A first half of a snap fastener 131 and a second half of a snap fastener 132 is affixed (by crimping, sewing, adhesive, or other fastening means) to the respective loose ends of second band 110 in a manner that allows the ends of second band 110 to be wrapped around a PCA pump control hand grip and held securely in place by mating the two halves of the snap fastener. The two halves of the snap fastener 131 and 132 may be reversed.

FIG. 4 shows the strap of the present invention fastened about a hand, with the loop tape 105 of a hook-and-loop fastener shown fastened to a hook tape, such as hook tape 106 shown in FIG. 2, thereby securing the first band 101 across the palm of a patient's hand or across the base of the fingers of a patient's hand. While a hook tape is not shown in FIG. 4, the stitching 106a used to sew the hook tape to the first band 101 is shown.

FIG. 5 illustrates another view of the strap of the present invention fastened about a hand with a PCA pump control hand grip 150 inserted through second loop 110. The strap may be positioned across the palm of the hand, or the base of the fingers, as the wearer prefers, so long as the PCA pump control button 151 is positioned in a manner that allows the wearer to easily press the button.

FIG. 6 shows a PCA pump control and the strap of the present invention, wherein the PCA pump control user is holding the hand grip of the PCA pump control in the palm of their hand, and is further depressing a PCA pump control button 151 to self-administer a dose of medicine.

FIG. 7 is an illustration of a front view of a strap for a PCA pump control. The strap is comprised of a first band 701 and a second band 710 that is affixed to the first band 701. A piece of a loop tape 705 of a hook-and-loop fastener is sewn to one end of the outside surface (the surface that does not contact the patient's hand) of the first band 701, and a piece of hook tape 706 is also sewn to the outside surface of the first band 701, but positioned between loop tape 705 and second band 710. It is understood that the positions of the loop tape 705 and the hook tape 706 of a hook-and-loop fastener may be reversed. A ring 720 is attached to the other end of first band 701. Ring 720 may comprise a rigid material such as molded plastic or other materials. The first band 701 may be made from any number of materials, but is preferably made from an elastic fabric material. In an alternate embodiment of the present invention, the first band may be made from an elastic loop tape, thereby eliminating the need to affix loop tape to the elastic first band 701. The second band 710 may also be made from any number of materials. In one embodiment of the present invention, the second band 710 is made from an elastic fabric formed into a loop and sewn to first band 701. In this view, the far end of first tape 701 passes through the ring 720 and folds back on first band 701, and stitching 720a fastens the far end of first band 701 to an adjacent region of first band 701 to hold ring 720 in place. Alternately, stitching 720a may be replaced by fabric welding.

In another embodiment, the second band 710 is made from an elastic fabric material, with one end sewn to the first band 701 and the other end loose. The loose end may have a piece of a loop tape of a hook-and-loop fastener that is sewn to the loose end of second band 710 that is suitably enabled to mate with a piece of hook tape that is sewn to the back side of first band 701. In another embodiment, the second band is made from an inelastic fabric material, with one end sewn to the first band 701 and the other end loose. The loose end may have one half of a snap fastener crimped to the loose end of second band 710 that is suitably enabled to mate with a matching snap fastener half that is crimped to the back side of first band 701.

In this view, the second band 710 is also shown affixed to the middle of the longitudinal length of the first band 701. It is understood that the positions of the loop tape 705 and hook tape 706 may be reversed.

FIG. 7A is an illustration of a side view of a strap for a PCA pump control. In this view, the strap is shown flat for illustrative purposes. In this view it may be seen more clearly that loop tape 705 and hook tape 706 of a hook-and-loop fastener and second loop 710 are affixed to the surface of first tape 701. In one embodiment of the present invention, loop tape 705, hook tape 706, and second loop 710 are affixed by sewing means; however, it is understood that other affixing means such as adhesives or fabric welding and the like may be used. In this view it can be seen more clearly that the far end of first tape 701 passes through the ring 720 and folds back on first band 701, and stitching 720a (or other fastening means) fastens the far end of first band 701 to an adjacent region of first band 701 to hold ring 720 in place.

FIG. 7B illustrates a second side view of the strap illustrated in FIGS. 7 and 7A. In this view, the strap is shown as it would be placed around a patient's hand. In this side view, the end of the strap with the loop fastener 705 has been pushed through the ring 720 and folded over. To adjust the strap, the end of the strap with the loop fastener 705 is pulled to snugly wrap the PCA pump control strap around the patient's hand. To fasten the strap in place, the loop fastener 705 is pressed against the hook fastener 706 to engage the components of the hook-and-loop fastener. In an alternate embodiment of the present invention, first tape 701 is made from elastic loop tape rather than plain elastic tape with a strip of hook or loop tape affixed to the end opposite ring 720. In this alternate embodiment, a strip of hook tape is affixed to the end of the first tape opposite the ring 720, and said hook tape can be pressed against the first tape 701 at any point in order to engage the components of the hook-and-loop fastener.

What is claimed is:

1. A strap for wrapping or slipping over a hand for holding a PCA pump control at or near a palm of the hand or a base of fingers of the hand, the strap comprising:
   an elasticized elongated band, at least a portion of which is comprised of a loop material of a hook-and-loop fastener;
   an elasticized continuous loop affixed to the elasticized elongated band, the elasticized continuous loop being sized to accommodate and retain the PCA pump control in a desired position;
   a strip including a hook material of the hook-and-loop fastener, the strip being affixed to a first end of the elasticized elongated band; and
   a ring affixed to a second end of the elasticized elongated band;
   wherein the strap is configured for securement about the hand by extending the strip of hook material through an opening of the ring so that the strip can be pulled taut and the hook material can be placed against a portion of the loop material of the elasticized elongated band, thereby allowing the strap to be secured about the hand and facilitating the PCA pump control being positioned at or near the calm of the hand or the base of the fingers of the hand; and
   wherein the elasticized continuous loop is affixed to the elasticized elongated band with fabric welding.

2. The strap of claim 1, wherein the ring is made from a plastic material.

3. The strap of claim 1, wherein the elasticized continuous loop is affixed to the elasticized elongated band at a location along a length of the elasticized elongated band that is intermediate of the first and second ends.

4. The strap of claim 3, wherein the elasticized continuous loop is affixed to the elasticized elongated band at a generally central location along the length of the elasticized elongated band.

5. A strap for wrapping or slipping over a hand for holding a PCA pump control at or near a palm of the hand or a base of fingers of the hand, the strap comprising:
   an elasticized elongated band, at least a portion of which is comprised of a loop material of a hook-and-loop fastener;
   an elasticized continuous loop affixed to the elasticized elongated band, the elasticized continuous loop being sized to accommodate and retain the PCA pump control in a desired position;
   a strip including a hook material of the hook-and-loop fastener, the strip being affixed to a first end of the elasticized elongated band; and
   a ring affixed to a second end of the elasticized elongated band;
   wherein the loop material, the hook material and the elasticized continuous loop all are affixed to a same surface of the elasticized elongated band;
   wherein the strap is configured for securement about the hand by extending the strip of hook material through an opening of the ring so that the strip can be pulled taut and the hook material can be placed against a portion of the loop material of the elasticized elongated band, thereby allowing the strap to be secured about the hand and facilitating the PCA pump control being positioned at or near the palm of the hand or the base of the fingers of the hand; and
   wherein an orientation of an opening defined by the elasticized continuous loop is transverse to an orientation of an opening defined by the elasticized elongated band when the strap is secured about the hand.

6. The strap of claim 5, wherein the elasticized continuous loop is affixed to the elasticized elongated band with stitching.

7. The strap of claim 5, wherein the ring is made from a plastic material.

8. The strap of claim 5, wherein the elasticized continuous loop is affixed to the elasticized elongated band at a location along a length of the elasticized elongated band that is intermediate of the first and second ends.

9. The strap of claim 8, wherein the elasticized continuous loop is affixed to the elasticized elongated band at a generally central location along the length of the elasticized elongated band.

10. The strap of claim 5, wherein the elasticized continuous loop is affixed to the elasticized elongated band with fabric welding.

11. A medical apparatus retention strap for wrapping or slipping over a hand, the medical apparatus retention strap comprising:
    an elasticized elongated band including a loop material of a hook-and-loop fastener;
    an elasticized continuous loop affixed to the elasticized elongated band, the elasticized continuous loop encircling a portion of a PCA pump control;
    a strip including a hook material of the hook-and-loop fastener, the strip being affixed to a first end of the elasticized elongated band; and
    a ring affixed to a second end of the elasticized elongated band;

wherein the medical apparatus retention strap is configured for securement about the hand by extending the strip of hook material through an opening of the ring so that the strip can be pulled taut and the hook material can be placed against the loop material of the elasticized elongated band, thereby allowing the medical apparatus retention strap to be secured about the hand; and wherein a diameter of the elasticized continuous loop is less than a cross-sectional thickness of the portion of the PCA pump control encircled by the elasticized continuous loop such that the PCA pump control is clenchingly retained in a desired position, thereby facilitating the PCA pump control being positioned at or near a palm of the hand or a base of fingers of the hand.

12. The medical apparatus retention strap of claim 11, wherein the ring is made from a plastic material.

13. The medical apparatus retention strap of claim 11, wherein the elasticized continuous loop is affixed to the elasticized elongated band at a location along a length of the elasticized elongated band that is intermediate of the first and second ends.

14. The medical apparatus retention strap of claim 13, wherein the elasticized continuous loop is affixed to the elasticized elongated band at a generally central location along the length of the elasticized elongated band.

15. The medical apparatus retention strap of claim 11, wherein the elasticized continuous loop is affixed to the elasticized elongated band with stitching.

16. The medical apparatus retention strap of claim 11, wherein an orientation of an opening defined by the elasticized continuous loop is transverse to an orientation of an opening defined by the elasticized elongated band when the medical apparatus retention strap is secured about the hand.

17. The medical apparatus retention strap of claim 11, wherein the elasticized continuous loop is affixed to the elasticized elongated band with fabric welding.

18. A method for retaining a PCA pump control at a desired position relative to a patient's hand, the method comprising:

providing a medical apparatus retention strap comprising:
an elasticized elongated band, at least a portion of which is comprised of a loop material of a hook-and-loop fastener;
an elasticized continuous loop affixed to the elasticized elongated band within a profile defined by a width of the elasticized elongated band;
a strip including a hook material of the hook-and-loop fastener, the strip being affixed to a first end of the elasticized elongated band; and
a ring affixed to a second end of the elasticized elongated band;

positioning the PCA pump control through the elasticized continuous loop;

positioning the medical apparatus retention strap adjacent the hand such that the PCA pump control is disposed at or near a palm of the hand or a base of fingers of the hand;

positioning the strip to extend fully through the ring, thereby arranging the elasticized elongated band into a loop shape about the hand;

pulling a distal end of the strip such that the loop shape is taut about the hand; and positioning the hook material of the elasticized continuous loop against a portion of the loop material of the elasticized elongated band, thereby attaching the strip to the elasticized elongated band and securing the medical apparatus retention strap about the hand;

whereby, upon securement of the medical apparatus retention strap about the hand, the PCA pump control is retained at or near the palm of the hand or the base of the fingers of the hand.

19. The method of claim 18, wherein the ring is made from a plastic material.

20. The method of claim 18, wherein a diameter of the elasticized continuous loop is less than a cross-sectional thickness of at least a portion of the PCA pump control such that the PCA pump control is clenchingly retained at or near the palm of the hand or the base of the fingers of the hand.

* * * * *